US011220435B1

(12) United States Patent
Ojo (10) Patent No.: US 11,220,435 B1
(45) Date of Patent: Jan. 11, 2022

(54) MOLECULAR SIEVE SSZ-94, CATALYST, AND METHODS OF USE THEREOF

(71) Applicant: CHEVRON U.S.A. INC., San Ramon, CA (US)

(72) Inventor: Adeola Florence Ojo, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 17/214,793

(22) Filed: Mar. 26, 2021

(51) Int. Cl.
| | |
|---|---|
| C01B 39/48 | (2006.01) |
| B01J 29/70 | (2006.01) |
| B01J 29/74 | (2006.01) |
| C07C 5/27 | (2006.01) |
| C01B 39/46 | (2006.01) |

(52) U.S. Cl.
CPC .......... C01B 39/48 (2013.01); B01J 29/7046 (2013.01); B01J 29/7492 (2013.01); C07C 5/2775 (2013.01); C01B 39/46 (2013.01); C01P 2002/72 (2013.01); C07C 2529/70 (2013.01); C07C 2529/74 (2013.01)

(58) Field of Classification Search
CPC ... C01B 39/48; C01P 2002/72; B01J 29/7046; B01J 29/7492; C07C 5/2775; C07C 2529/70; C07C 2529/74
See application file for complete search history.

(56) References Cited

PUBLICATIONS

Lee et al., "Characteristics of Magnesium-Promoted Pt/ZSM-23 Catalyst for the Hydroisomerization of n-Hexadecane", Ind. Eng. Chem. Res. 2013, 52, 15359-15365 (Year: 2013).*
Lee et al., "Hydroisomerization and hydrocracking over platinum loaded ZSM-23 catalysts in the presence of sulfur and nitrogen compoundsfor the dewaxing of diesel fuel", /Fuel 134 (2014) 237-243 (Year: 2014).*

* cited by examiner

Primary Examiner — David M Brunsman
(74) Attorney, Agent, or Firm — Mark Warzel (57) ABSTRACT

The present application pertains to family of new crystalline molecular sieves designated SSZ-94. Molecular sieve SSZ-94 is structurally similar to sieves falling within the MTT structure type such as SSZ-32x, SSZ-32, ZSM-23, EU-13, ISI-4, and KZ-1 family of molecular sieves. SSZ-94 is characterized as having magnesium.

24 Claims, 4 Drawing Sheets

MOLECULAR SIEVE SSZ-94, CATALYST, AND METHODS OF USE THEREOF

TECHNICAL FIELD

The present disclosure relates to catalysts having an MTT type structure with magnesium oxide referred to as molecular sieve SSZ-94 and methods of use thereof.

BACKGROUND AND SUMMARY

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures and acid site properties, providing enhanced selectivities and activities in these processes.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types" Sixth Revised Edition, Elsevier (2007) Molecular sieves are periodically ordered in three dimensions. Structurally disordered structures show periodic ordering in dimensions less than three (i.e., in two, one or zero dimensions). This phenomenon is characterized as stacking disorder of structurally invariant Periodic Building Units (PerBuU). Crystal structures built from Periodic Building Units are called end-member structures if periodic ordering is achieved in all three dimensions. Disordered structures are those where the stacking sequence of the Periodic Building Units deviates from periodic ordering up to statistic stacking sequences.

Molecular sieves having a MTT-type framework code have a one-dimensional 10-ring pore system. MTT-type molecular sieves have very similar, but not identical, X-ray diffraction patterns. SSZ-32 and its small crystal variant, SSZ-32x, are known MTT-type molecular sieves.

SSZ-32 and methods for making it are disclosed in U.S. Pat. Nos. 5,707,600; 5,053,373; 5,300,210; and 5,397,454 which are incorporated herein by reference.

It has now been found that by using the manufacturing methods described herein below, a novel molecular sieve designated herein as SSZ-94 is achieved.

The present disclosure is directed to a family of crystalline molecular sieves with unique properties and a MTT-type topology, referred to herein as "molecular sieve SSZ-94" or simply "SSZ-94."

Advantageously, the present application pertains in one embodiment to a molecular sieve comprising an MTT-type framework, a mole ratio of from about 15 to about 100 of silicon oxide to aluminum oxide, a total micropore volume of between 0.02 and 0.05 cc/g, an external surface area of between 80 and 120 m$^2$/g; and magnesium.

In another embodiment the present application pertains to a process for converting hydrocarbons, comprising contacting a hydrocarbonaceous feed under hydrocarbon converting conditions with a catalyst. The catalyst comprises a molecular sieve comprising an MTT-type framework, a mole ratio of from about 15 to about 100 of silicon oxide to aluminum oxide, a total micropore volume of between 0.02 and 0.05 cc/g, an external surface area of between 80 and 120 m$^2$/g and magnesium. In some embodiments the selectivity is improved over comparable catalysts lacking magnesium.

Further features of the disclosed molecular sieve and the advantages offered thereby are explained in greater detail hereinafter with reference to specific example embodiments illustrated in the accompanying drawings.

DETAILED DESCRIPTION

Although illustrative embodiments of one or more aspects are provided herein, the disclosed processes may be implemented using any number of techniques. The disclosure is not limited to the illustrative or specific embodiments, drawings, and techniques illustrated herein, including any exemplary designs and embodiments illustrated and described herein, and may be modified within the scope of the appended claims along with their full scope of equivalents.

Unless otherwise indicated, the following terms, terminology, and definitions are applicable to this disclosure. If a term is used in this disclosure but is not specifically defined herein, the definition from the IUPAC Compendium of Chemical Terminology, 2nd ed (1997), may be applied, provided that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein is to be understood to apply.

"API gravity" refers to the gravity of a petroleum feedstock or product relative to water, as determined by ASTM D4052-11.

"Viscosity index" (VI) represents the temperature dependency of a lubricant, as determined by ASTM D2270-10 (E2011).

"Vacuum gas oil" (VGO) is a byproduct of crude oil vacuum distillation that can be sent to a hydroprocessing unit or to an aromatic extraction for upgrading into base oils. VGO generally comprises hydrocarbons with a boiling range distribution between 343° C. (649° F.) and 593° C. (1100° F.) at 0.101 MPa.

"Treatment," "treated," "upgrade," "upgrading" and "upgraded," when used in conjunction with an oil feedstock, describes a feedstock that is being or has been subjected to hydroprocessing, or a resulting material or crude product, having a reduction in the molecular weight of the feedstock, a reduction in the boiling point range of the feedstock, a reduction in the concentration of asphaltenes, a reduction in the concentration of hydrocarbon free radicals, and/or a reduction in the quantity of impurities, such as sulfur, nitrogen, oxygen, halides, and metals.

"Hydroprocessing" refers to a process in which a carbonaceous feedstock is brought into contact with hydrogen and a catalyst, at a higher temperature and pressure, for the purpose of removing undesirable impurities and/or converting the feedstock to a desired product. Examples of hydroprocessing processes include hydrocracking, hydrotreating, catalytic dewaxing, and hydrofinishing.

"Hydrocracking" refers to a process in which hydrogenation and dehydrogenation accompanies the cracking/fragmentation of hydrocarbons, e.g., converting heavier hydrocarbons into lighter hydrocarbons, or converting aromatics and/or cycloparaffins (naphthenes) into non-cyclic branched paraffins.

"Hydrotreating" refers to a process that converts sulfur and/or nitrogen-containing hydrocarbon feeds into hydrocarbon products with reduced sulfur and/or nitrogen content, typically in conjunction with hydrocracking, and which generates hydrogen sulfide and/or ammonia (respectively) as byproducts. Such processes or steps performed in the presence of hydrogen include hydrodesulfurization, hydrodenitrogenation, hydrodemetallation, and/or hydrodearomatization of components (e.g., impurities) of a hydrocarbon feedstock, and/or for the hydrogenation of unsaturated compounds in the feedstock. Depending on the type of hydrotreating and the reaction conditions, products of hydrotreating processes may have improved viscosities, viscosity indices, saturates content, low temperature properties, volatilities and depolarization, for example. The terms "guard layer" and "guard bed" may be used herein synonymously and interchangeably to refer to a hydrotreating catalyst or hydrotreating catalyst layer. The guard layer may be a component of a catalyst system for hydrocarbon dewaxing, and may be disposed upstream from at least one hydroisomerization catalyst.

"Catalytic dewaxing", or hydroisomerization, refers to a process in which normal paraffins are isomerized to their more branched counterparts by contact with a catalyst in the presence of hydrogen.

"Hydrofinishing" refers to a process that is intended to improve the oxidation stability, UV stability, and appearance of the hydrofinished product by removing traces of aromatics, olefins, color bodies, and solvents. UV stability refers to the stability of the hydrocarbon being tested when exposed to UV light and oxygen. Instability is indicated when a visible precipitate forms, usually seen as Hoc or cloudiness, or a darker color develops upon exposure to ultraviolet light and air. A general description of hydrofinishing may be found in U.S. Pat. Nos. 3,852,207 and 4,673,487.

The term "Hydrogen" or "hydrogen" refers to hydrogen itself, and/or a compound or compounds that provide a source of hydrogen.

"Cut point" refers to the temperature on a True Boiling Point (TBP) curve at which a predetermined degree of separation is reached.

"Pour point" refers to the temperature at which an oil will begin to flow under controlled conditions. The pour point may be determined by, for example, ASTM D5950.

"Cloud point" refers to the temperature at which a lube base oil sample begins to develop a haze as the oil is cooled under specified conditions. The cloud point of a lube base oil is complementary to its pour point. Cloud point may be determined by, for example, ASTM D5773.

"TBP" refers to the boiling point of a hydrocarbonaceous feed or product, as determined by Simulated Distillation (SimDist) by ASTM D2887-13.

"Hydrocarbonaceous", "hydrocarbon" and similar terms refer to a compound containing only carbon and hydrogen atoms. Other identifiers may be used to indicate the presence of particular groups, if any, in the hydrocarbon (e.g., halogenated hydrocarbon indicates the presence of one or more halogen atoms replacing an equivalent number of hydrogen atoms in the hydrocarbon).

The term "Periodic Table" refers to the version of the IUPAC Periodic Table of the Elements dated Jun. 22, 2007, and the numbering scheme for the Periodic Table Groups is as described in Chem. Eng. News, 63(5), 26-27 (1985). "Group 2" refers to IUPAC Group 2 elements, e.g., magnesium, (Mg), Calcium (Ca), Strontium (Sr), Barium (Ba) and combinations thereof in any of their elemental, compound, or ionic form. "Group 6" refers to IUPAC Group 6 elements, e.g., chromium (Cr), molybdenum (Mo), and tungsten (W). "Group 7" refers to IUPAC Group 7 elements, e.g., manganese (Mn), rhenium (Re) and combinations thereof in any of their elemental, compound, or ionic form. "Group 8" refers to IUPAC Group 8 elements, e.g., iron (Fe), ruthenium (Ru), osmium (Os) and combinations thereof in any of their elemental, compound, or ionic form. "Group 9" refers to IUPAC Group 9 elements, e.g., cobalt (Co), rhodium (Rh), iridium (Ir) and combinations thereof in any of their elemental, compound, or ionic form. "Group 10" refers to IUPAC Group 10 elements, e.g., nickel (Ni), palladium (Pd), platinum (Pt) and combinations thereof in any of their elemental, compound, or ionic form. "Group 14" refers to IUPAC Group 14 elements, e.g., germanium (Ge), tin (Sn), lead (Pb) and combinations thereof in any of their elemental, compound, or ionic form.

The term "support", particularly as used in the term "catalyst support", refers to conventional materials that are typically a solid with a high surface area, to which catalyst materials are affixed. Support materials may be inert or participate in the catalytic reactions, and may be porous or non-porous. Typical catalyst supports include various kinds of carbon, alumina, silica, and silica-alumina, e.g., amorphous silica aluminates, zeolites, alumina-boria, silica-alumina-magnesia, silica-alumina-titania and materials obtained by adding other zeolites and other complex oxides thereto.

"Molecular sieve" refers to a material having uniform pores of molecular dimensions within a framework structure, such that only certain molecules, depending on the type of molecular sieve, have access to the pore structure of the molecular sieve, while other molecules are excluded, e.g., due to molecular size and/or reactivity. The term "molecular sieve" and "zeolite" are synonymous and include (a) intermediate and (b) final or target molecular sieves and molecular sieves produced by (1) direct synthesis or (2) post-crystallization treatment (secondary modification). Secondary synthesis techniques allow for the synthesis of a target material from an intermediate material by heteroatom lattice substitution or other techniques. For example, an aluminosilicate can be synthesized from an intermediate borosilicate by post-crystallization heteroatom lattice substitution of the Al for B. Such techniques are known, for example as described in U.S. Pat. No. 6,790,433. Zeolites, crystalline aluminophosphates and crystalline silicoaluminophosphates are representative examples of molecular sieves.

The term "MTT molecular sieve" includes all molecular sieves and their isotypes that have been assigned the International Zeolite Associate framework code MTT, as described in the Atlas of Zeolite Framework Types, eds. Ch. Baerlocher, L. B. McCusker and D. H. Olson, Elsevier, 6.sup.th revised edition, 2007.

In this disclosure, while compositions and methods or processes are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "an alkali metal" is meant to encompass one, or mixtures or combinations of more than one, transition metal or alkali metal, unless otherwise specified.

All numerical values within the detailed description and the claims herein are modified by "about" or "approximately" the indicated value, and take into account experimental error and variations that would be expected by a person having ordinary skill in the art.

In one aspect, the present invention is a hydroisomerization catalyst system, useful to make dewaxed products including base/lube oils, the catalyst comprising a catalyst composition comprising an SSZ-94 molecular sieve. The catalyst composition may be arranged in conjunction with other catalysts such that a hydrocarbon feedstock may be sequentially contacted with either the hydroisomerization catalyst composition first to provide a first product followed by contacting the first product with the other catalyst composition(s) to provide a second product, or with the other catalyst composition(s) first followed by contacting one or more product streams from such other catalysts with the hydroisomerization catalyst. The hydroisomerization catalyst composition generally comprises an SSZ-94 molecular sieve, along with other components, including, e.g., matrix (support) materials and at least one modifier selected from Groups 6 to 10 and Group 14 of the Periodic Table and magnesium.

In a further aspect, the present invention concerns a hydroisomerization process, useful to make dewaxed products including base oils, the process comprising contacting a hydrocarbon feedstock with the hydroisomerization catalyst system under hydroisomerization conditions to produce a base oil product or product stream. As noted, the feedstock may be first contacted with the hydroisomerization catalyst composition to provide a first product followed by contacting the first product with one or more other catalyst compositions as needed to produce a second product, or may be first contacted with such other catalyst compositions as needed, followed by contacting one or more product streams from such catalyst compositions with the hydroisomerization catalyst. The first and/or second products from such arrangements may themselves be a base oil product, or may be used to make a base oil product.

SSZ-94 Molecular Sieves Comprising Magnesium

The SSZ-94 molecular sieve used herein is made in a similar manner to SSZ-32 except that SSZ-94 comprises magnesium, preferably as part of the reaction mixture as opposed to impregnated after molecular sieve formation. Methods for synthesizing MTT-type molecular sieves like SSZ-32 are described in U.S. Pat. Nos. 5,707,600; 5,053,373; 5,300,210; and 5,397,454 which patents are incorporated herein by reference. Useful molecular sieves herein generally comprise an MTT-type framework, a mole ratio of from about 15 to about 100 of silicon oxide to aluminum oxide, a total micropore volume of between 0.02 and 0.05 cc/g, an external surface area of between 80 and 120 m$^2$/g; and magnesium. Molecular sieve SSZ-94 is structurally similar to sieves falling within the MTT structure type such as SSZ-32x, SSZ-32, ZSM-23, EU-13, ISI-4, and KZ-1 family of molecular sieves and is characterized as comprising magnesium.

Magnesium Amounts and Addition

As described above, the primary difference between SSZ-94 and SSZ-32 is that SSZ-94 comprises magnesium. The magnesium may be added at any convenient point during the process of making the molecular sieve. In some embodiments, magnesium oxide is added to the reaction mixture for forming the molecular sieve although other sources of magnesium may be employed. The source of magnesium is not critical so long as magnesium becomes part of the molecular sieve to afford it the desired properties. For example, magnesium salts such as magnesium nitrate, sulfate, chloride and even mixed magnesium and calcium salts may be employed.

The amount of magnesium may vary depending upon the desired selectivity, conversion, and/or base oil properties such as lube yield, viscosity index, gas make, and the like.

In some embodiments, the molecular sieve comprises a magnesium oxide to silicon dioxide ratio of at least about 0.005, or at least about 0.01, or at least about 0.04, or at least about 0.05 up to about 0.4, or up to about 0.25, or up to about 0.22, or up to about 0.2.

SSZ-94 Reaction Mixture Components

Typical and preferred molar ratios for reaction mixture components are described in the table below. M is selected from Groups 1 and 2 of the Periodic Table and Q is a hexamethonium cation. The mixtures are heated, stirred, filtered, washed, and dried as described in the MTT structure references incorporated by reference above and in the examples below.

| REACTION MIXTURE | | |
|---|---|---|
| Reactants | Typical Molar Ratio | Preferred Molar Ratio |
| SiO$_2$/Al$_2$O$_3$ | 15-100 | 25-50 |
| M/SiO$_2$ | 0.05-0.4 | 0.075-0.3 |
| MgO/SiO$_2$ | 0.005-0.4 | 0.01-0.25 |
| Q/SiO$_2$ | 0.05-0.5 | 0.10-0.30 |
| OH$^-$/SiO$_2$ | 0.1-0.4 | 0.15-0.30 |
| H$_2$O/SiO$_2$ | 10-300 | 10-70 |

In some embodiments the molecular sieve further comprises palladium, platinum, or a mixture thereof. The molecular sieve of the present application may differ from SSZ-32 in regard to, for example, how it behaves in an ammonia temperature programmed desorption test and in its FTIR spectra.

Matrix and Modifiers

The SSZ-94 molecular sieves of the catalyst composition is generally combined with a matrix material to form a base material. The base material may, e.g., be formed as a base extrudate by combining the molecular sieve with the matrix material, extruding the mixture to form shaped extrudates, followed by drying and calcining of the extrudate. The catalyst composition also typically further comprises at least one modifier selected from Groups 6 to 10 and Group 14, and optionally further comprising a Group 2 metal, of the Periodic Table. Modifiers may be added through the use of impregnation solutions comprising modifier compounds.

Suitable matrix materials for the catalyst composition include alumina, silica, ceria, titania, tungsten oxide, zirconia, or a combination thereof. In some embodiments, aluminas for the catalyst compositions and the process may also be a "high nanopore volume" alumina, abbreviated as "HNPV" alumina, as described in U.S. application Ser. No. 17/095,010, filed on Nov. 11, 2020, herein incorporated by reference. Suitable aluminas are commercially available, including, e.g., Catapal® aluminas and Pural® aluminas from Sasol or Versal® aluminas from UOP. In general, the alumina can be any alumina known for use as a matrix material in a catalyst base. For example, the alumina can be boehmite, bayerite, γ-alumina, η-alumina, θ-alumina, δ-alumina, χ-alumina, or a mixture thereof.

Suitable modifiers are selected from Groups 6-10 and Group 14 of the Periodic Table (IUPAC). Suitable Group 6 modifiers include Group 6 elements, e.g., chromium (Cr), molybdenum (Mo), and tungsten (W) and combinations thereof in any of their elemental, compound, or ionic form. Suitable Group 7 modifiers include Group 7 elements, e.g., manganese (Mn), rhenium (Re) and combinations thereof in any of their elemental, compound, or ionic form. Suitable Group 8 modifiers include Group 8 elements, e.g., iron (Fe), ruthenium (Ru), osmium (Os) and combinations thereof in any of their elemental, compound, or ionic form. Suitable Group 9 modifiers include Group 9 elements, e.g., cobalt (Co), rhodium (Rh), iridium (Ir) and combinations thereof in any of their elemental, compound, or ionic form. Suitable Group 10 modifiers include Group 10 elements, e.g., nickel (Ni), palladium (Pd), platinum (Pt) and combinations thereof in any of their elemental, compound, or ionic form. Suitable Group 14 modifiers include Group 14 elements, e.g., germanium (Ge), tin (Sn), lead (Pb) and combinations thereof in any of their elemental, compound, or ionic form. In addition, optional Group 2 modifiers may be present, including Group 2 elements, e.g., magnesium, (Mg), Calcium (Ca), Strontium (Sr), Barium (Ba) and combinations thereof in any of their elemental, compound, or ionic form.

The modifier advantageously comprises one or more Group 10 metals. The Group 10 metal may be, e.g., platinum, palladium or a combination thereof. Platinum is a suitable Group 10 metal along with another Groups 6 to 10 and Group 14 metal in some aspects. While not limited thereto, the Groups 6 to 10 and Group 14 metal may be more narrowly selected from Pt, Pd, Ni, Re, Ru, Ir, Sn, or a combination thereof. In conjunction with Pt as a first metal in the first and/or second catalyst compositions, an optional second metal in the catalyst composition may also be more narrowly selected from the Groups 6 to 10 and Group 14 metals, such as, e.g., Pd, Ni, Re, Ru, Ir, Sn, or a combination thereof. In a more specific instance, the catalyst may comprise Pt as a Group 10 metal in an amount of 0.01-5.0 wt. % or 0.01-2.0 wt. %, or 0.1-2.0 wt. %, more particularly 0.01-1.0 wt. % or 0.3-0.8 wt. %. An optional second metal selected from Pd, Ni, Re, Ru, Ir, Sn, or a combination thereof as a Group 6 to 10 and Group 14 metal may be present, in an amount of 0.01-5.0 wt. % or 0.01-2.0 wt. %, or 0.1-2.0 wt. %, more particularly 0.01-1.0 wt. % and 0.01-1.5 wt. %.

The metals content in the catalyst composition may be varied over useful ranges, e.g., the total modifying metals content for the catalyst may be 0.01-5.0 wt. % or 0.01-2.0 wt. %, or 0.1-2.0 wt. % (total catalyst weight basis). In some instances, the catalyst composition comprises 0.1-2.0 wt. % Pt as one of the modifying metals and 0.01-1.5 wt. % of a second metal selected from Groups 6 to 10 and Group 14, or 0.3-1.0 wt. % Pt and 0.03-1.0 wt. % second metal, or 0.3-1.0 wt. % Pt and 0.03-0.8 wt. % second metal. In some cases, the ratio of the first Group 10 metal to the optional second metal selected from Groups 6 to 10 and Group 14 may be in the range of 5:1 to 1:5, or 3:1 to 1:3, or 1:1 to 1:2, or 5:1 to 2:1, or 5:1 to 3:1, or 1:1 to 1:3, or 1:1 to 1:4. In more specific cases, the catalyst composition comprises 0.01 to 5.0 wt. % of the modifying metal, 1 to 99 wt. % of the matrix material, and 0.1 to 99 wt. % of the molecular sieves.

The base extrudate may be made according to any suitable method. For example, the base extrudate may be made and then dried and calcined, followed by loading of any modifiers onto the base extrudate. Suitable impregnation techniques may be used to disperse the modifiers onto the base extrudate. The method of making the base extrudate is not intended to be particularly limited according to specific process conditions or techniques, however.

While not limited thereto, exemplary process conditions may include cases wherein the SSZ-94 molecular sieve, any added matrix material and any added liquid are mixed together at about 20 to 80° C. for about 0.5 to 30 min.; the extrudate is formed at about 20 to 80° C. and dried at about 90-150° C. for 0.5-8 hrs; the extrudate is calcined at 260-649° C. (500-1200° F.), in the presence of sufficient air flow, for 0.1-10 hours; the extrudate is impregnated with a modifier by contacting the extrudate with the metal impregnation solution containing at least one modifier for 0.1-10 hrs at a temperature in the range of about 20 to 80° C.; and the metal loaded extrudate is dried at about 90-150° C. for 0.1-10 hrs and calcined at 260-649° C. (500-1200° F.), in the presence of sufficient air flow, for 0.1-10 hours.

Process for Converting Hydrocarbons

In some embodiments the application pertains to a process for converting hydrocarbons using a catalyst comprising an SSZ-94 molecular sieve described herein. Generally, the process comprises contacting a hydrocarbonaceous feed under hydrocarbon converting conditions with a catalyst comprising the SSZ-94 molecular sieve. That is, the molecular sieve belongs to the MTT structure type family of zeolites such as SZ-32x, SSZ-32, ZSM-23, EU-13, ISI-4, and KZ-1. The SSZ-94 molecular sieve generally comprises an MTT-type framework, a mole ratio of from about 15 to about 100 of silicon oxide to aluminum oxide, a total micropore volume of between 0.02 and 0.05 cc/g, an external surface area of between 80 and 120 m$^2$/g, and magnesium.

There may be a number of advantages to employing SSZ-94 including, for example, at least about 1.5%, or at least about 3%, or at least about 3.5%, or at least about 4.5%, or at least about 6%, or at least about 8%, or at least about 10%, or even at least about 12% or more better selectivity at 96% isomerization conversion than a comparable process employing a comparable catalyst such as SSZ-32 or other MTT molecular sieve that lacks magnesium. In addition to the surprising and unexpected selectivity, processes employing SSZ-94 may provide improved lube yield (greater than about 0.3 weight percent, or greater than about 0.45 weight percent, or greater than about 0.6% up to 0.8% weight percent or more), better viscosity index (at least about 1, or at least about 2, or at least about 3, up to about 4, or up to about 5 or more), and/or improved gas make (reduced gas by at least about 0.2 weight percent, or at least about 0.3 weight percent up to about 0.4, or up to 1 weight percent or more) than a comparable process employing a comparable catalyst such as SSZ-32 that lacks magnesium.

Hydrocarbon Feed

The hydrocarbon feed may generally be selected from a variety of base oil feedstocks, and advantageously comprises gas oil; vacuum gas oil; long residue; vacuum residue; atmospheric distillate; heavy fuel; oil; wax and paraffin; used oil; deasphalted residue or crude; charges resulting from thermal or catalytic conversion processes; shale oil; cycle oil; animal and vegetable derived fats, oils and waxes;

petroleum and slack wax; or a combination thereof. The hydrocarbon feed may also comprise a feed hydrocarbon cut in the distillation range from 400–1300° F., or 500–1100° F., or 600–1050° F., and/or wherein the hydrocarbon feed has a KV100 (kinematic viscosity at 100° C.) range from about 3 to 30 cSt or about 3.5 to 15 cSt.

In some cases, the process may be used advantageously for a light or heavy neutral base oil feedstock, such as a vacuum gas oil (VGO), as the hydrocarbon feed where the SSZ-94 catalyst composition includes a Pt modifying metal, or a combination of Pt with another modifier.

The product(s), or product streams, may be used to produce one or more base oil products, e.g., to produce multiple grades having a KV100 in the range of about 2 to 30 cSt. Such base oil products may, in some cases, have a pour point of not more than about −12° C., or −15° C., or −20° C.

The hydroisomerization catalyst and process may also be combined with additional process steps, or system components, e.g., the feedstock may be further subjected to hydrotreating conditions with a hydrotreating catalyst prior to contacting the hydrocarbon feedstock with the hydroisomerization catalyst composition, optionally, wherein the hydrotreating catalyst comprises a guard layer catalyst comprising a refractory inorganic oxide material containing about 0.1 to 1 wt. % Pt and about 0.2 to 1.5 wt. % Pd.

In practice, hydrodewaxing is used primarily for reducing the pour point and/or for reducing the cloud point of the base oil by removing wax from the base oil. Typically, dewaxing uses a catalytic process for processing the wax, with the dewaxer feed is generally upgraded prior to dewaxing to increase the viscosity index, to decrease the aromatic and heteroatom content, and to reduce the amount of low boiling components in the dewaxer feed. Some dewaxing catalysts accomplish the wax conversion reactions by cracking the waxy molecules to lower molecular weight molecules. Other dewaxing processes may convert the wax contained in the hydrocarbon feed to the process by wax isomerization, to produce isomerized molecules that have a lower pour point than the non-isomerized molecular counterparts. As used herein, isomerization encompasses a hydroisomerization process, for using hydrogen in the isomerization of the wax molecules under catalytic hydroisomerization conditions.

Suitable hydrodewaxing conditions generally depend on the feed used, the catalyst used, desired yield, and the desired properties of the base oil. Typical conditions include a temperature of from 500° F. to 775° F. (260° C. to 413° C.); a pressure of from 300 psig to 3000 psig (2.07 MPa to 20.68 MPa gauge); a LHSV of from 0.25 hr$^{-1}$ to 20 hr$^{-1}$; and a hydrogen to feed ratio of from 2000 SCF/bbl to 30,000 SCF/bbl (356 to 5340 m$^3$ H$_2$/m$^3$ feed). Generally, hydrogen will be separated from the product and recycled to the isomerization zone. Generally, dewaxing processes of the present invention are performed in the presence of hydrogen. Typically, the hydrogen to hydrocarbon ratio may be in a range from about 2000 to about 10,000 standard cubic feet H$_2$ per barrel hydrocarbon, and usually from about 2500 to about 5000 standard cubic feet H$_2$ per barrel hydrocarbon. The above conditions may apply to the hydrotreating conditions of the hydrotreating zone as well as to the hydroisomerization conditions of the first and second catalyst. Suitable dewaxing conditions and processes are described in, e.g., U.S. Pat. Nos. 5,135,638; 5,282,958; and 7,282,134.

While the catalyst system and process has been generally described in terms of the hydroisomerization catalyst composition comprising the SSZ-94 molecular sieve, it should be understood that additional catalysts, including layered catalysts and treatment steps may be present, e.g., including, hydrotreating catalyst(s)/steps, guard layers, and/or hydrofinishing catalyst(s)/steps.

Typical and preferred molar ratios for reaction mixture components are described in the table below. The mixtures are heated, stirred, filtered, washed, and dried as described in the references incorporated by reference above and the example below. That is, suitable methods may comprise: (a) preparing a reaction mixture containing: at least one source of silicon, at least one source of aluminum, at least one source of an element selected from Groups 1 and 2 of the Periodic Table, at least one source of magnesium, hydroxide ions, hexamethonium cations, and water; and (b) subjecting the reaction mixture to crystallization conditions sufficient to form crystals of the molecular sieve. Suitable reaction mixtures are below. M is selected from Groups 1 and 2 of the Periodic Table and Q is a hexamethonium cation.

| REACTION MIXTURE | | |
|---|---|---|
| Reactants | Typical Molar Ratio | Preferred Molar Ratio |
| SiO$_2$/Al$_2$O$_3$ | 15-100 | 25-50 |
| M/SiO$_2$ | 0.05-0.4 | 0.075-0.3 |
| MgO/SiO$_2$ | 0.005-0.4 | 0.01-0.25 |
| Q/SiO$_2$ | 0.05-0.5 | 0.10-0.30 |
| OH$^-$/SiO$_2$ | 0.1-0.4 | 0.15-0.30 |
| H$_2$O/SiO$_2$ | 10-300 | 10-70 |

EXAMPLE EMBODIMENTS

1. A molecular sieve comprising an MTT-type framework, a mole ratio of from about 15 to about 100 of silicon oxide to aluminum oxide, a total micropore volume of between 0.02 and 0.05 cc/g, external surface area of between 80 and 120 m$^2$/g and magnesium.

2. The molecular sieve of embodiment 1, wherein the molecular sieve comprises a magnesium oxide to silicon dioxide ratio of from about 0.005 to about 0.4.

3. The molecular sieve of any preceding embodiment, wherein the molecular sieve comprises a magnesium oxide to silicon dioxide ratio of from about 0.01 to about 0.25.

4. The molecular sieve of any preceding embodiment, wherein the molecular sieve comprises a magnesium oxide to silicon dioxide ratio of from about 0.04 to about 0.22.

5. The molecular sieve of any preceding embodiment, wherein the molecular sieve comprises a magnesium oxide to silicon dioxide ratio of from about 0.05 to about 0.2.

6. The molecular sieve of any preceding embodiment, wherein the molecular sieve has a silicon oxide to aluminum oxide mole ratio of 25-50.

7. The molecular sieve of any preceding embodiment, wherein the molecular sieve is a product of a reaction mixture comprising a molar ratio of SiO$_2$/Al$_2$O$_3$ of from about 15 to about 100, of M/SiO$_2$ of from about 0.05 to about 0.4, of Q/SiO$_2$ of from about 0.05 to about 0.5, of OH/SiO$_2$ of from about 0.1 to about 0.4, of MgO/SiO$_2$ of from 0.005 to about 0.4 and of H$_2$O/SiO$_2$ of from about 10 to about 300 wherein M is selected from Groups 1 and 2 of the Periodic Table and Q is a hexamethonium cation.

8. The molecular sieve of any preceding embodiment, wherein the molecular sieve is a product of a reaction mixture comprising a molar ratio of SiO$_2$/Al$_2$O$_3$ of from about 25 to about 50, of M/SiO$_2$ of from about 0.075 to about 0.3, of Q/SiO$_2$ of from about 0.1 to about 0.30, of OH/SiO$_2$ of from about 0.15 to about 0.30, of MgO/SiO$_2$ of from 0.01 to about 0.25 and of H$_2$O/SiO$_2$ of from about 10 to about 70 wherein M is selected from Groups 1 and 2 of the Periodic Table and Q is a hexamethonium cation.

9. The molecular sieve of any preceding embodiment, which further comprises palladium, platinum, or a mixture thereof.

10. The molecular sieve of any preceding embodiment, wherein the molecular sieve has an external surface area between 80 and 110 m$^2$/g.

11. A method of preparing the molecular sieve of any preceding embodiment, comprising: (a) preparing a reaction mixture containing at least one source of silicon, at least one source of aluminum, at least one source of an element selected from Groups 1 and 2 of the Periodic Table, at least one source of magnesium, hydroxide ions, hexamethonium cations, and water; and (b) subjecting the reaction mixture to crystallization conditions sufficient to form crystals of the molecular sieve.

12. The method of embodiment 11 wherein the molecular sieve is prepared from a reaction mixture comprising a molar ratio of SiO$_2$/Al$_2$O$_3$ of from about 15 to about 100, of M/SiO$_2$ of from about 0.05 to about 0.4, of Q/SiO$_2$ of from about 0.05 to about 0.5, of OH/SiO$_2$ of from about 0.1 to about 0.4, of MgO/SiO$_2$ of from 0.005 to about 0.4 and of H$_2$O/SiO$_2$ of from about 10 to about 300 wherein M is selected from Groups 1 and 2 of the Periodic Table and Q is a hexamethonium cation 13. The method of embodiment 11 or any subsequent embodiment wherein the molecular sieve is prepared from a reaction mixture comprising a molar ratio of SiO$_2$/Al$_2$O$_3$ of from about 25 to about 50, of M/SiO$_2$ of from about 0.075 to about 0.3, of Q/SiO$_2$ of from about 0.1 to about 0.30, of OH/SiO$_2$ of from about 0.15 to about 0.30, of MgO/SiO$_2$ of from 0.01 to about 0.25 and of H$_2$O/SiO$_2$ of from about 10 to about 70 wherein M is selected from Groups 1 and 2 of the Periodic Table and Q is a hexamethonium cation.

14. A process for converting hydrocarbons, comprising contacting a hydrocarbonaceous feed under hydrocarbon converting conditions with a catalyst comprising a molecular sieve, the molecular sieve comprising an MTT-type framework, a mole ratio of from about 15 to about 100 of silicon oxide to aluminum oxide, a total micropore volume of between 0.02 and 0.05 cc/g, an external surface area of between 80 and 120 m$^2$/g, and magnesium.

15. The process of embodiment 14, wherein the molecular sieve comprises a magnesium oxide to silicon dioxide ratio of from about 0.005 to about 0.4.

16. The process of embodiment 14 or any subsequent embodiment, wherein the molecular sieve comprises a magnesium oxide to silicon dioxide ratio of from about 0.01 to about 0.25.

17. The process of embodiment 14 or any subsequent embodiment, wherein the molecular sieve comprises a magnesium oxide to silicon dioxide ratio of from about 0.04 to about 0.22.

18. The process of embodiment 14 or any subsequent embodiment, wherein the molecular sieve comprises a magnesium oxide to silicon dioxide ratio of from about 0.05 to about 0.2.

19. The process of embodiment 14 or any subsequent embodiment, wherein the molecular sieve has a silicon oxide to aluminum oxide mole ratio of 25 to 50.

20. The process of embodiment 14 or any subsequent embodiment, wherein the process has at least 3% better selectivity at 96% isomerization conversion than a comparable process employing a comparable catalyst that lacks magnesium.

21. The process of embodiment 14 or any subsequent embodiment, wherein the process has at least 6% better selectivity at 96% isomerization conversion than a comparable process employing a comparable catalyst that lacks magnesium.

22. A method of preparing molecular sieve SSZ-94, comprising:
(a) preparing a reaction mixture comprising:
(i) at least one active source of silicon;
(ii) at least one active source of aluminum;
(iii) at least one active source of magnesium;
(iv) at least one active source of an alkali metal;
(v) hydroxide ions; and
(vi) an organic templating agent consisting of at least one small, neutral amine capable of forming the zeolite, said amine containing four to about eight carbon atoms and (a) only carbon, nitrogen and hydrogen atoms, (b) one primary, secondary or tertiary, but not quaternary, amino group, and (c) a tertiary nitrogen atom, or at least one tertiary carbon atom, or a nitrogen atom bonded directly to at least one secondary carbon atom;
(b) maintaining the reaction mixture under conditions sufficient to form crystals of the zeolite wherein the zeolite is prepared in the absence of an amine component.
(c) recovering the crystals of the zeolite, 23. The method of embodiment 22, wherein the reaction mixture has a composition in terms of mole ratios falling within the ranges below:

| | |
|---|---|
| SiO$_2$/Al$_2$O$_3$ molar ratio | 15-100 |
| H$_2$O/SiO$_2$ molar ratio | 5-100 |
| OH$^-$/SiO2 molar ratio | 0.07-1.0 |
| M/SiO$_2$ molar ratio | 0.05-0.5 |
| MgO/SiO$_2$ molar ratio | 0.005-0.4 |
| Q/SiO$_2$ molar ratio | 0.02-0.5 | wherein:
M is an alkali metal cation; and Q is the organic templating agent.

24. The method of embodiment 23, wherein the reaction mixture has a composition in terms of mole ratios falling within the ranges below:

| | |
|---|---|
| SiO$_2$/Al$_2$O$_3$ molar ratio | 20-50 |
| H$_2$O/SiO$_2$ molar ratio | 20-50 |
| OH$^-$/SiO2 molar ratio | 0.15-0.3 |
| M/SiO$_2$ molar ratio | 0.075-0.3 |
| MgO/SiO$_2$ molar ratio | 0.005-0.4 |
| Q/SiO$_2$ molar ratio | 0.1-0.3 | wherein:
M is an alkali metal cation; and Q is the organic templating agent.

25. The method of embodiment 23 or any subsequent embodiment, wherein the H$_2$O/SiO$_2$ molar ratio is 15-20.

26. The method of embodiment 22 or any subsequent embodiment, wherein the at least one active source of an oxide of silicon, the at least one active source of an oxide of aluminum and the at least one active source of an oxide of magnesium are derived from a common source.

27. The method of embodiment 22 or any subsequent embodiment, wherein the conditions sufficient to form crystals of the zeolite comprises heating the reaction mixture to a temperature of from 140° C. to 170° C. for a suitable period of time to form crystals of the zeolite.

28. The method of embodiment 22 or any subsequent embodiment, wherein the organic templating agent is N-methyl-N'-isopropyl imidazolium hydroxide.

29. The process of embodiment 22 or any subsequent embodiment, wherein the small, neutral amine is selected from the group consisting of isobutylamine, diisobutylamine, diisopropylamine, sec-butylamine, 2,5-dimethylpyrrolidine and 2,6-dimethylpiperidine.

30. The method of embodiment 22 or any subsequent embodiment, wherein the zeolite has, in the as-synthesized form, a mole ratio of silicon oxide to aluminum oxide of 20:1 to less than 40:1.

31. The method according to embodiment 22 or any subsequent embodiment, wherein the zeolite has, in the calcined form, an X-ray diffraction pattern substantially as shown in the following Table:

| 2-Theta[a] (Degrees) | d-spacing (Angstroms) | Relative Absolute Intensity (%)[b] |
|---|---|---|
| 8.11 | 10.888 | m |
| 8.80 | 10.045 | w |
| 11.32 | 7.813 | m |
| 14.64 | 6.046 | vw |
| 15.85 | 5.588 | vw |
| 16.32 | 5.427 | vw |
| 18.09 | 4.899 | w |
| 19.67 | 4.510 | vs |
| 20.93 | 4.241 | vs |
| 21.61 | 4.109 | m |
| 22.85 | 3.890 | vs |
| 24.04 | 3.699 | vs |
| 24.64 | 3.610 | vs |
| 25.21 | 3.530 | s |
| 25.96 | 3.430 | s |
| 27.03 | 3.296 | w |
| 28.27 | 3.155 | w |
| 29.38 | 3.037 | vw |
| 29.94 | 2.983 | vw |
| 31.59 | 2.830 | w |
| 33.10 | 2.704 | vw |
| 34.03 | 2.632 | vw |
| 35.49 | 2.527 | s |
| 36.51 | 2.459 | w |
| 37.77 | 2.380 | w |
| 38.52 | 2.335 | w |

[a]±0.20
[b]The powder XRD patterns provided are based on a relative intensity scale in which the strongest line in the X-ray pattern is assigned a value of 100: vw = very weak (>0 to <10); w = weak (10 to ≤20); m = medium (>20 to ≤40); s = strong (>40 to ≤60); vs = very strong (>60 to ≤100)

Example 1

67.36 g (45.4%) of potassium hydroxide were dissolved in 1435.88 g of water. 12.65 g of Barcroft 0250 alumina was added and the mixture was stirred to dissolve all the solids. 409.34 g of Nyacol 2040-NH$_4$ colloidal silica was then added, followed by 6.25 g of SSZ-32 seed crystals. The resulting mixture was stirred as 50.384 g of isobutylamine (Aldrich, 99%) was added. Finally, 16.97 g of Magnesium Oxide (Fisher Chemical™ M68-500) was added to the reaction liner. The liner was transferred to a 1-gallon autoclave.

| Components | Molar ratio |
|---|---|
| SiO$_2$/Al$_2$O$_3$ | 41.8 |
| H$_2$O/SiO$_2$ | 34.0 |
| OH$^-$/SiO$_2$ | 0.194 |
| M/SiO$_2$ | 0.194 |
| Q/SiO$_2$ | 0.243 |
| MgO/SiO$_2$ | 0.15 |
| % Seed | 2.91% |

Figure 1:
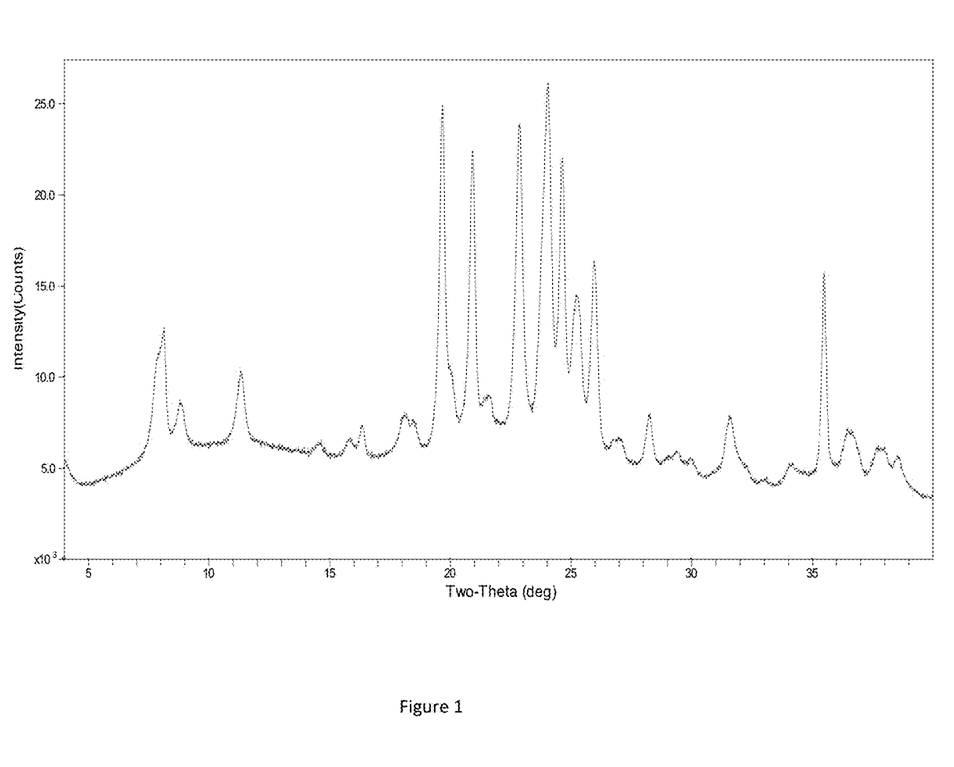
FIG. 1 depicts an XRD powder diffraction of an SSZ-94 material of Example 1.
Figure 2:
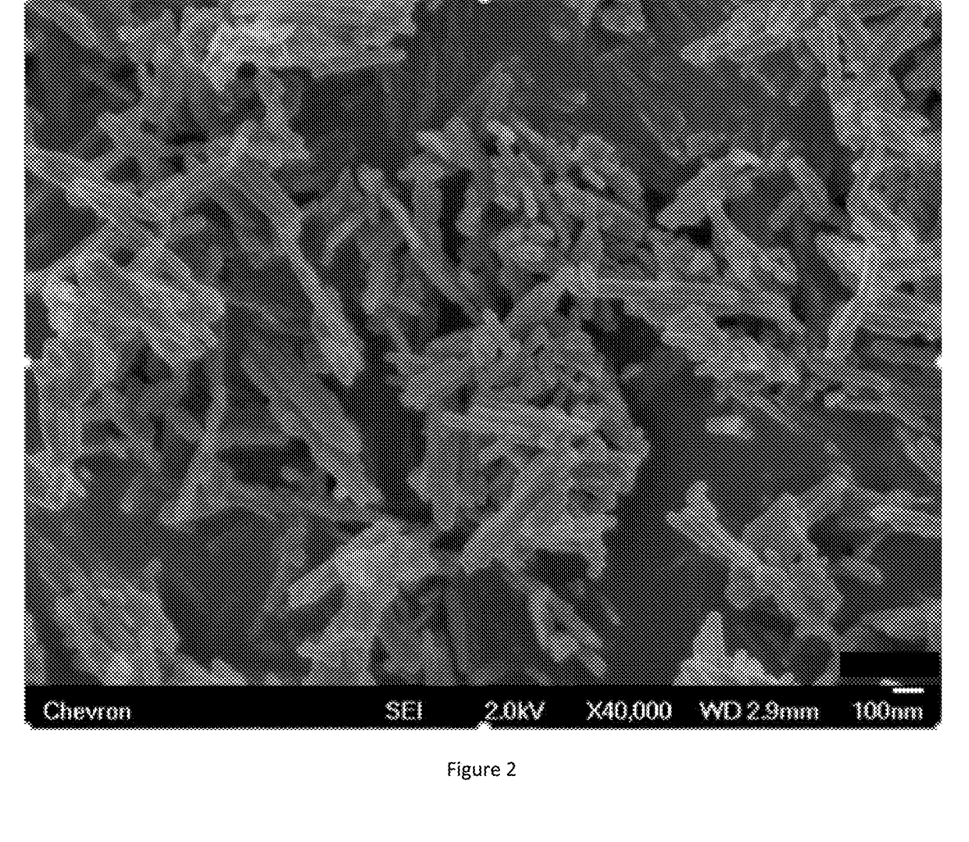
FIG. 2 depicts an SEM of an SSZ-94 material of Example 1.

The reaction mixture was heated to 170° C. over a period of 8 hours and continuously stirred at 150 rpm. The endpoint was found to be 45 hours. The product was filtered, washed with deionized water, and dried at 95° C. (203° F.). The as-synthesized product was determined by XRD powder diffraction (FIG. 1) to be SSZ-94 type material. The SEM of the as-synthesized SSZ-94 product (FIG. 2) showed the product was composed of small hexagonal crystals up to about 0.35 µm. Analysis of Al, K, Si, and Mg by ICP revealed 2.03%, 1.73%, 34.8%, and 4.95% respectively having a Mg/Si molar ratio of 0.164 and SiO$_2$/Al$_2$O$_3$ molar ratio of 32.9.

The as-synthesized product was converted into the ammonium form by first calcining in air at 545° C. for 3 hours and then 595° C. for 3 hours followed by two ion exchanges with ammonium nitrate solution at 95° C. for at least 4 hours, and dried at 95° C. (203° F.). The calcined material retained its full X-ray crystallinity. The resulting ammonium exchanged product contained 3.29% Mg with Mg/Si molar ratio of 0.10, SiO$_2$/Al$_2$O$_3$ molar ratio of 31.9, micropore volume of 0.0394 cc/g, external surface area of 100.23 m$^2$/g and BET surface area of 186.15 m$^2$/g.

Example 2 (Comparative)—Similar to Nakagawa U.S. Pat. No. 5,707,600

An example of a product without magnesium oxide was prepared.

A reaction mixture for the synthesis of SSZ-32 was prepared following Example 1 in the absence of magnesium oxide. The molar ratios of the reaction mixture components were:

| Components | Molar ratio |
|---|---|
| SiO$_2$/Al$_2$O$_3$ | 42.0 |
| H$_2$O/SiO$_2$ | 35.0 |
| OH$^-$/SiO$_2$ | 0.20 |
| KOH/SiO$_2$ | 0.20 |
| Q/SiO$_2$ | 0.25 |
| % Seed | 3.0% |

Figure 3:
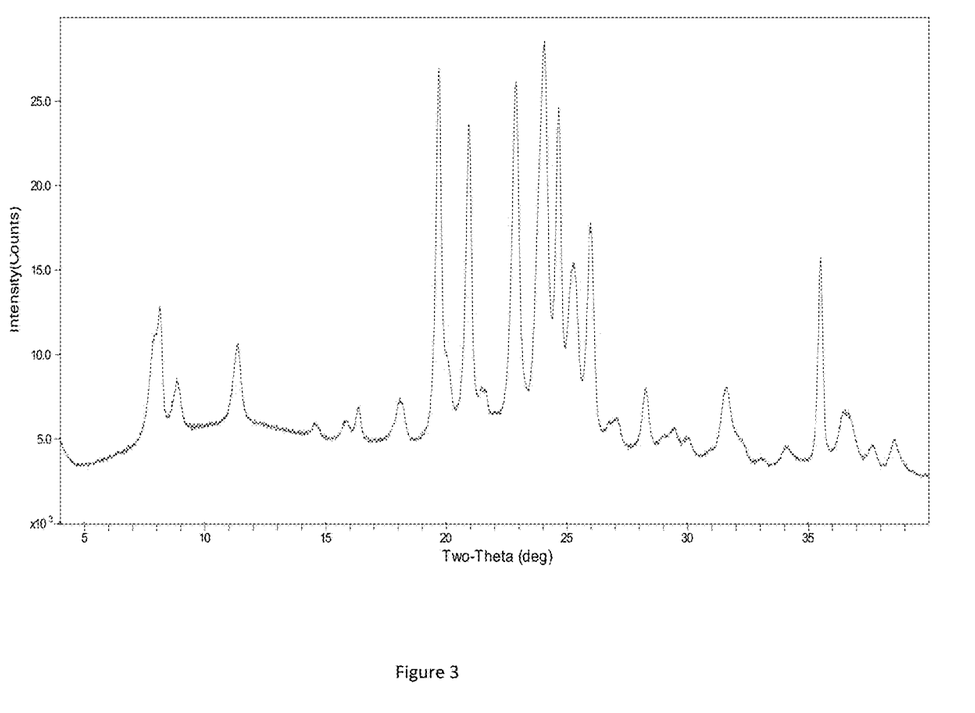
FIG. 3 depicts an XRD powder diffraction of an SSZ-32 material of Comparative Example 2.
Figure 4:
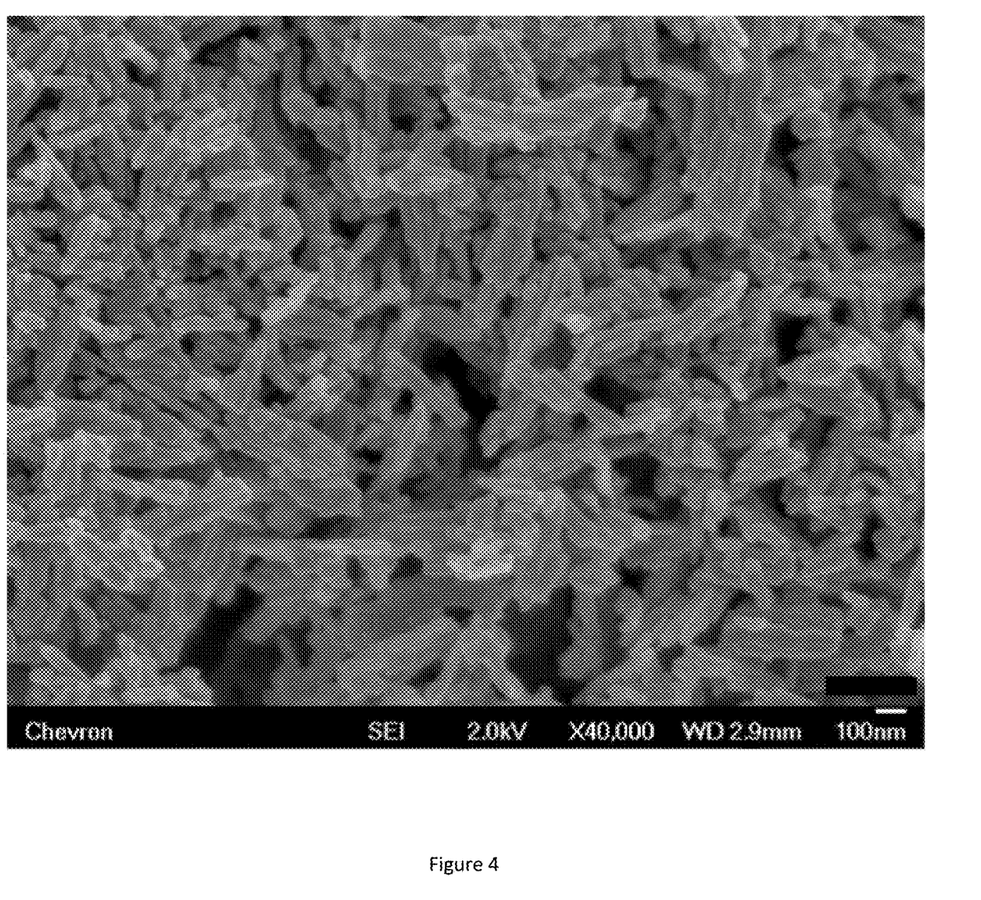
FIG. 4 depicts an SEM of an SSZ-32 material of Comparative Example 2.

The crystallization follows procedure in Example 1. The endpoint was found to be 52 hours. The product was filtered, washed with deionized water and dried at 95° C. (203° F.). The as-synthesized product was determined by XRD powder diffraction (FIG. 3) to be SSZ-32. The SEM of the as-synthesized SSZ-32 product (FIG. 4) showed the product was composed of small hexagonal crystals up to 0.26 µm. Analysis of Al, K, and Si by ICP revealed 2.47%, 2.06%, and 39.5% respectively having SiO$_2$/AL$_2$O$_3$ molar ratio of 30.7.

The as-synthesized product was converted into the ammonium form by first calcining in air at 545° C. for 3 hours and then 595° C. for 3 hours followed by two ion exchanges with ammonium nitrate solution at 95° C. for at least 4 hours, and dried at 95° C. (203° F.). The calcined material retained its X-ray crystallinity. The calcined material retained its full X-ray crystallinity. The resulting ammonium exchanged product contained SiO$_2$/AL$_2$O$_3$ molar ratio of 31.9, micropore volume of 0.0632 cc/g, external surface area of 42.67 m$^2$/g and BET surface area of 179.20 m$^2$/g.

Catalyst Preparation and Evaluation

Hydroprocessing Tests: n-Hexadecane Isomerization

Example 3

The surprising information concerning this invention described here came from the testing of isomerization selectivity using n-hexadecane as feed and Pd metal on the product from Example 1 of the instant invention.

Palladium ion-exchange was carried out on the ammonium-exchanged samples from Examples 1 and 2 using tetraamminepalladium(II) nitrate (0.5 wt % Pd). After ion-exchange, the samples were dried at 95° C. and then calcined in air at 482° C. for 3 hours to convert the tetraamminepalladium(II) nitrate to palladium oxide.

0.5 g of each of the palladium exchanged samples from Examples 1 and 2 was loaded in the center of a 23 inch-long by 0.25 inch outside diameter stainless steel reactor tube with alundum loaded upstream of the catalyst for pre-heating the feed (total pressure of 1200 psig; down-flow hydrogen rate of 160 mL/min (when measured at 1 atmosphere pressure and 25° C.); down-flow liquid feed rate of 1 mL/hour. All materials were first reduced in flowing hydrogen at about 315° C. for 1 hour. Products were analyzed by on-line capillary gas chromatography (GC) once every thirty minutes. Raw data from the GC was collected by an automated data collection/processing system and hydrocarbon conversions were calculated from the raw data.

The catalyst was tested at about 260° C. initially to determine the temperature range for the next set of measurements. The overall temperature range will provide a wide range of hexadecane conversion with the maximum conversion just below and greater than 96%. At least five on-line GC injections were collected at each temperature. Conversion was defined as the amount of hexadecane reacted to produce other products (including iso-n-C$_{16}$ isomers). Yields were expressed as weight percent of products other than n-C$_{16}$ and included iso-C$_{16}$ as a yield product.

The results are summarized in the Table 2. The isomerization selectivity at 96% conversion for the Magnesium containing molecular sieve SSZ-94 of the present invention (Examples 1) is surprisingly better than that of Magnesium free comparative Example 2. Equally important is the desirable low C$_4$ cracking, the gas make, of the SSZ-94 composition is better than in the comparative example. Showing presence of the Magnesium oxide in the reaction mixture during zeolite synthesis of SSZ-94 is necessary to achieve the improved performance characteristics exhibited by SSZ-94.

TABLE 2

| Examples | Example 1 | Example 2 |
| --- | --- | --- |
| Selectivity % | 78% | 66% |
| Temperature ° F. | 579 | 513 |
| C$_4^-$ Cracking | 3.5% | 5.1% |

The present disclosure is not to be limited in terms of the particular embodiments described in this application, which are intended as illustrations of various aspects. Many modifications and variations can be made without departing from its spirit and scope, as may be apparent. Functionally equivalent methods and systems within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only, and is not intended to be limiting.

The foregoing description, along with its associated embodiments, has been presented for purposes of illustration only. It is not exhaustive and does not limit the invention to the precise form disclosed. Those skilled in the art may appreciate from the foregoing description that modifications and variations are possible in light of the above teachings or may be acquired from practicing the disclosed embodiments. For example, the steps described need not be performed in the same sequence discussed or with the same degree of separation. Likewise, various steps may be omitted, repeated, or combined, as necessary, to achieve the same or similar objectives. Accordingly, the invention is not limited to the above-described embodiments, but instead is defined by the appended claims in light of their full scope of equivalents.

In the preceding specification, various preferred embodiments have been described with references to the accompanying drawings. It may, however, be evident that various modifications and changes may be made thereto, and additional embodiments may be implemented, without departing from the broader scope of the invention as set forth in the claims that follow. The specification and drawings are accordingly to be regarded as an illustrative rather than restrictive sense.

What is claimed is:

1. A molecular sieve comprising an MTT-type framework, a mole ratio of from about 15 to about 100 of silicon oxide to aluminum oxide, a total micropore volume of between 0.02 and 0.05 cc/g, external surface area of between 80 and 120 m$^2$/g and magnesium.

2. The molecular sieve of claim 1, wherein the molecular sieve comprises a magnesium oxide to silicon dioxide ratio of from about 0.005 to about 0.4.

3. The molecular sieve of claim 1, wherein the molecular sieve comprises a magnesium oxide to silicon dioxide ratio of from about 0.01 to about 0.25.

4. The molecular sieve of claim 1, wherein the molecular sieve comprises a magnesium oxide to silicon dioxide ratio of from about 0.04 to about 0.22.

5. The molecular sieve of claim 1, wherein the molecular sieve comprises a magnesium oxide to silicon dioxide ratio of from about 0.05 to about 0.2.

6. The molecular sieve of claim 1, wherein the molecular sieve has a silicon oxide to aluminum oxide mole ratio of 25-50.

7. The molecular sieve of claim 1, wherein the molecular sieve is a product of a reaction mixture comprising a molar ratio of SiO$_2$/Al$_2$O$_3$ of from about 15 to about 100, of M/SiO$_2$ of from about 0.05 to about 0.4, of Q/SiO$_2$ of from about 0.05 to about 0.5, of OH/SiO$_2$ of from about 0.1 to about 0.4, of MgO/SiO$_2$ of from 0.005 to about 0.4, and of H$_2$O/SiO$_2$ of from about 10 to about 300, wherein M is selected from Groups 1 and 2 of the Periodic Table and Q is a hexamethonium cation.

8. The molecular sieve of claim 1, wherein the molecular sieve is a product of a reaction mixture comprising a molar ratio of SiO$_2$/Al$_2$O$_3$ of from about 25 to about 50, of M/SiO$_2$ of from about 0.075 to about 0.3, of Q/SiO$_2$ of from about 0.1 to about 0.30, of OH/SiO$_2$ of from about 0.15 to about 0.30, of MgO/SiO$_2$ of from about 0.01 to about 0.25, and of H$_2$O/SiO$_2$ of from about 10 to about 70 wherein M is selected from Groups 1 and 2 of the Periodic Table and Q is a hexamethonium cation.

9. The molecular sieve of claim 1, which further comprises palladium, platinum, or a mixture thereof.

10. The molecular sieve of claim 1, wherein the molecular sieve has an external surface area of between 80 and 110 m$^2$/g.

11. A method of preparing the molecular sieve of claim 1, comprising: (a) preparing a reaction mixture containing: at least one source of silicon, at least one source of aluminum, at least one source of an element selected from Groups 1 and 2 of the Periodic Table, at least one source of magnesium, hydroxide ions, hexamethonium cations, and water; and (b) subjecting the reaction mixture to crystallization conditions sufficient to form crystals of the molecular sieve.

12. The method of claim 11 wherein the molecular sieve is prepared from a reaction mixture comprising a molar ratio of SiO$_2$/Al$_2$O$_3$ of from about 15 to about 100, of M/SiO$_2$ of from about 0.05 to about 0.4, of Q/SiO$_2$ of from about 0.05 to about 0.5, of OH/SiO$_2$ of from about 0.1 to about 0.4, of MgO/SiO$_2$ of from 0.005 to about 0.4 and of H$_2$O/SiO$_2$ of from about 10 to about 300 wherein M is selected from Groups 1 and 2 of the Periodic Table and Q is a hexamethonium cation.

13. The method of claim 11 wherein the molecular sieve is prepared from a reaction mixture comprising a molar ratio of SiO$_2$/Al$_2$O$_3$ of from about 25 to about 50, of M/SiO$_2$ of from about 0.075 to about 0.3, of Q/SiO$_2$ of from about 0.1 to about 0.30, of OH/SiO$_2$ of from about 0.15 to about 0.30, of MgO/SiO$_2$ of from about 0.01 to about 0.25 and of H$_2$O/SiO$_2$ of from about 10 to about 70 wherein M is selected from Groups 1 and 2 of the Periodic Table and Q is a hexamethonium cation.

14. A process for converting hydrocarbons, comprising contacting a hydrocarbonaceous feed under hydrocarbon converting conditions with a catalyst comprising a molecular sieve, the molecular sieve comprising an MTT-type framework, a mole ratio of from about 15 to about 100 of silicon oxide to aluminum oxide, a total micropore volume of between 0.02 and 0.05 cc/g, an external surface area of between 80 and 120 m$^2$/g, and magnesium.

15. The process of claim 14, wherein the molecular sieve comprises a magnesium oxide to silicon dioxide ratio of from about 0.005 to about 0.4.

16. The process of claim 14, wherein the molecular sieve comprises a magnesium oxide to silicon dioxide ratio of from about 0.01 to about 0.25.

17. The process of claim 14, wherein the molecular sieve comprises a magnesium oxide to silicon dioxide ratio of from about 0.04 to about 0.22.

18. The process of claim 14, wherein the molecular sieve comprises a magnesium oxide to silicon dioxide ratio of from about 0.05 to about 0.2.

19. The process of claim 14, wherein the molecular sieve has a silicon oxide to aluminum oxide mole ratio of 25 to 50.

20. The process of claim 14, wherein the process has at least 3% better selectivity at 96% isomerization conversion than a comparable process employing a comparable catalyst that lacks magnesium.

21. The process of claim 14, wherein the process has at least 6% better selectivity at 96% isomerization conversion than a comparable process employing a comparable catalyst that lacks magnesium.

22. A method of preparing molecular sieve SSZ-94, comprising:
(a) preparing a reaction mixture comprising:
 (i) at least one active source of silicon;
 (ii) at least one active source of aluminum;
 (iii) at least one active source of magnesium;
 (iv) at least one active source of an alkali metal;
 (v) hydroxide ions; and
 (vi) an organic templating agent consisting of at least one small, neutral amine capable of forming the zeolite, said amine containing four to about eight carbon atoms and (a) only carbon, nitrogen, and hydrogen atoms, (b) one primary, secondary or tertiary, but not quaternary, amino group, and (c) a tertiary nitrogen atom, or at least one tertiary carbon atom, or a nitrogen atom bonded directly to at least one secondary carbon atom;
(b) maintaining the reaction mixture under conditions sufficient to form crystals of the zeolite wherein the zeolite is prepared in the absence of an amine component;
(c) recovering the crystals of the zeolite.

23. The method of claim 22, wherein the reaction mixture has a composition in terms of mole ratios falling within the ranges below:

| | |
|---|---|
| SiO$_2$/Al$_2$O$_3$ molar ratio | 15-100 |
| H$_2$O/SiO$_2$ molar ratio | 5-100 |
| OH$^-$/SiO2 molar ratio | 0.07-1.0 |
| M/SiO$_2$ molar ratio | 0.05-0.5 |
| MgO/SiO$_2$ molar ratio | 0.005-0.4 |
| Q/SiO$_2$ molar ratio | 0.02-0.5 | wherein:
M is an alkali metal cation; and
Q is the organic templating agent.

24. The method according to claim 22, wherein the zeolite has, in the calcined form, an X-ray diffraction pattern substantially as shown in the following Table:

| 2-Theta$^{(a)}$ (Degrees) | d-spacing (Angstroms) | Relative Absolute Intensity (%)$^{(b)}$ |
|---|---|---|
| 8.11 | 10.888 | m |
| 8.80 | 10.045 | w |
| 11.32 | 7.813 | m |
| 14.64 | 6.046 | vw |
| 15.85 | 5.588 | vw |
| 16.32 | 5.427 | vw |
| 18.09 | 4.899 | w |
| 19.67 | 4.510 | vs |
| 20.93 | 4.241 | vs |
| 21.61 | 4.109 | m |
| 22.85 | 3.890 | vs |
| 24.04 | 3.699 | vs |
| 24.64 | 3.610 | vs |
| 25.21 | 3.530 | s |
| 25.96 | 3.430 | s |
| 27.03 | 3.296 | w |
| 28.27 | 3.155 | w |
| 29.38 | 3.037 | vw |
| 29.94 | 2.983 | vw |
| 31.59 | 2.830 | w |
| 33.10 | 2.704 | vw |
| 34.03 | 2.632 | vw |
| 35.49 | 2.527 | s |

-continued

| 2-Theta$^{(a)}$ (Degrees) | d-spacing (Angstroms) | Relative Absolute Intensity (%)$^{(b)}$ |
|---|---|---|
| 36.51 | 2.459 | w |
| 37.77 | 2.380 | w |
| 38.52 | 2.335 | w. |

$^{(a)}$±0.20
$^{(b)}$The powder XRD patterns provided are based on a relative intensity scale in which the strongest line in the X-ray pattern is assigned a value of 100: vw = very weak (>0 to <10); w = weak (10 to ≤20); m = medium (>20 to ≤40); s = strong (>40 to ≤60); vs = very strong (>60 to ≤100)

\* \* \* \* \*